United States Patent
Fritz et al.

(10) Patent No.: US 9,072,866 B2
(45) Date of Patent: *Jul. 7, 2015

(54) CEREBROSPINAL FLUID EVALUATION SYSTEM HAVING THERMAL FLOW AND FLOW RATE MEASUREMENT PAD USING A PLURALITY OF CONTROL SENSORS

(71) Applicant: Neuro Diagnostic Devices, Inc., Bensalem, PA (US)

(72) Inventors: Frederick J. Fritz, Skillman, NJ (US); Marek Swoboda, Philadelphia, PA (US)

(73) Assignee: Neuro Diagnostic Devices, Inc., Princeton, NJ (US)

( * ) Notice: Subject to any disclaimer, the term of this patent is extended or adjusted under 35 U.S.C. 154(b) by 127 days.

This patent is subject to a terminal disclaimer.

(21) Appl. No.: 14/013,644

(22) Filed: Aug. 29, 2013

(65) Prior Publication Data
US 2014/0005589 A1   Jan. 2, 2014

Related U.S. Application Data

(63) Continuation of application No. 12/936,162, filed as application No. PCT/US2009/039146 on Apr. 1, 2009, now Pat. No. 8,551,011, application No. 14/013,644, (Continued)

(51) Int. Cl.
*A61M 27/00* (2006.01)
*G01F 1/684* (2006.01)
(Continued)

(52) U.S. Cl.
CPC ........... *A61M 27/006* (2013.01); *G01F 1/6847* (2013.01); *A61B 5/031* (2013.01); *A61B 5/14507* (2013.01); *A61B 2562/0271* (2013.01); *A61B 2562/043* (2013.01)

(58) Field of Classification Search
CPC .......... A61B 5/01; A61B 5/031; A61B 5/032; G01F 1/684; G01F 1/688; G01F 1/6847

USPC ......................................................... 600/549
See application file for complete search history.

(56) References Cited

U.S. PATENT DOCUMENTS 4,548,516 A * 10/1985 Helenowski .................. 374/135
5,255,979 A * 10/1993 Ferrari ........................... 374/158
(Continued)

FOREIGN PATENT DOCUMENTS

JP    07-275210    10/1995
JP    10-276993    10/1998
(Continued)

OTHER PUBLICATIONS

Stein, et al., "A Noninvasive Approach to Quantitive Measurement of Flow Through CSF Shunts," J. Neurosurg., vol. 54, Apr. 1981.
(Continued)

*Primary Examiner* — Sean Dougherty
*Assistant Examiner* — Michael C Stout
(74) *Attorney, Agent, or Firm* — Caesar Rivise, PC (57) ABSTRACT

A method and device for testing for the presence, absence and/or rate of flow in a shunt tubing implanted under the skin by using a measurement pad having a plurality of temperature sensors, one of which is aligned with the shunt and the other sensors being symmetrically displaced on either side of the first temperature sensor in a direction transverse to the shunt tubing. These "outer" temperature sensors act as control temperature sensors. A temperature source, e.g., a cooling agent, positioned within an insulated enclosure, is then applied at a predetermined location on the measurement pad that is insulated from the temperature sensors. The movement of this temperature "pulse" is detected by the shunt-aligned temperature sensor via the shunt tubing as the CSF carries the temperature pulse while the control sensors detect the pulse via convection through the skin. The temperature data from these sensors are provided to a CSF analyzer that determines a CSF shunt flow status or flow rate.

10 Claims, 5 Drawing Sheets

Related U.S. Application Data filedwhich is a continuation of application No. 12/055,990, on Mar. 26, 2008, now abandoned.

(60) Provisional application No. 61/042,496, filed on Apr. 4, 2008, provisional application No. 60/989,284, filed on Nov. 20, 2007, provisional application No. 60/941,827, filed on Jun. 4, 2007, provisional application No. 60/939,205, filed on May 21, 2007, provisional application No. 60/911,687, filed on Apr. 13, 2007.

(51) Int. Cl.
*A61B 5/03* (2006.01)
*A61B 5/145* (2006.01)

(56) References Cited

U.S. PATENT DOCUMENTS

| | | | |
|---|---|---|---|
| 7,520,862 | B2 | 4/2009 | Neff |
| 7,625,117 | B2 | 12/2009 | Haslett et al. |
| 8,075,470 | B2 | 12/2011 | Alekseyenko et al. |
| 8,302,471 | B2 | 11/2012 | Van Der Wiel |
| 8,551,011 | B2 * | 10/2013 | Fritz et al. ............ 600/549 |
| 8,894,584 | B2 * | 11/2014 | Swoboda et al. ....... 600/549 |
| 2002/0035340 | A1 * | 3/2002 | Fraden et al. .......... 600/549 |
| 2002/0121137 | A1 * | 9/2002 | Fujiwara et al. ....... 73/204.26 |
| 2003/0004495 | A1 | 1/2003 | Saul |
| 2004/0068201 | A1 | 4/2004 | Saul |
| 2004/0147871 | A1 | 7/2004 | Burnett |
| 2005/0094707 | A1 | 5/2005 | Lee et al. |
| 2005/0149170 | A1 | 7/2005 | Tassel et al. |
| 2005/0171452 | A1 | 8/2005 | Neff |
| 2005/0204811 | A1 | 9/2005 | Neff |
| 2006/0000271 | A1 | 1/2006 | Bork |
| 2006/0235349 | A1 | 10/2006 | Osborn et al. |
| 2007/0073132 | A1 | 3/2007 | Vosch |
| 2007/0206655 | A1 | 9/2007 | Haslett et al. |
| 2007/0282218 | A1 | 12/2007 | Yarden |
| 2008/0039739 | A1 | 2/2008 | Buja |
| 2008/0150682 | A1 | 6/2008 | Shii |
| 2008/0207984 | A1 | 8/2008 | Alekseyenko et al. |
| 2008/0214951 | A1 | 9/2008 | Fritz et al. |
| 2010/0228179 | A1 | 9/2010 | Thomas et al. |
| 2011/0054382 | A1 | 3/2011 | Fritz et al. |

FOREIGN PATENT DOCUMENTS

| | | |
|---|---|---|
| JP | 2004-513681 | 5/2004 |
| JP | 2006-017722 | 1/2006 |
| JP | 2008-032544 | 2/2008 |
| JP | 2009-189815 | 8/2009 |
| WO | WO 02/007596 | 7/2002 |
| WO | WO 2008-127867 | 10/2008 |
| WO | WO 2009-146075 | 12/2009 |
| WO | WO 2011-150323 | 12/2011 |

OTHER PUBLICATIONS

International Search Report for corresponding PCT Application No. PCT/US2009/039146, dated Oct. 1, 2009.
International Search Report for related PCT Application No. PCT/US2011/037218 dated Jan. 10, 2012.
International Search Report for related PCT Application No. PCT/US2011/038317 dated Feb. 24, 2012.
International Search Report for related PCT Application No. PCT/US2013/052018 dated Nov. 6, 2013.
International Search Report for related PCT Application No. PCT/US2013/071928 dated Mar. 6, 2014.
Bech-Azeddine, et al., "Idiopathic Normal-Pressure Hydrocephalus: Clinical Comorbidity Corrected With Cerebrospinal With Cerebral Biopsy Findings and Outcome of Cerebrospinal Fluid Shunting", Journal of Neurology, Neurosurgery & Psychiatry, vol. 78, pp. 157-161, 2007.
Cohen, M., "Measurement of the Thermal Properties of Human Skin. A Review", The Journal of Investigative Dermatology, vol. 69, No. 3, pp. 333-338, 1977.
Drake J., et al., "Cerebrospinal Fluid Flow Dynamics in Children with External Ventricular Drains", Neurosurgery, vol. 28, No. 2, pp. 242-250, 1991.
Drake, J., et al., "Randomized Trial of Cerebrospinal Fluid Shunt Calve Design in Pediatric Hydrocephalus", Neurosurgery, vol. 43, Issue 2, pp. 1-39, Aug. 1998.
Eggleston, T., et al., "Comparison of Two Porcine (*Sus scrofa domestica*) Skin Models for in Vivo Near-Infrared Laser Exposure", Comparative Medicine, vol. 50, No. 4, pp. 391-397, Aug. 2000.
Hidaka M., et al., "Dynamic Measurement of the Flow Rate in Cerebrospinal Fluid Shunts in Hydrocephalic Patients", European Journal of Nuclear Medicine, vol. 28, No. 7, pp. 888-893, Jul. 2001.
Iskandar, B., et al., "Death in Shunted Hydrocephalic Children in the 1990s", Pediatric Neurosurgery, vol. 28, pp. 173-176, Apr. 1998.
Iskandar, B., et al., "Pitfalls in the Diagnosis of Ventricular Shunt Dysfunction: Radiology Reports and Ventricular Size", Pediatrics, vol. 101, No. 6, pp. 1031-1036, Jun. 1998.
Kestle, J., et al., "Lack of Benefit of Endoscopic Ventriculoperitoneal Shunt Insertion: A Multicenter Randomized Trial", Journal of Neurosurgery, vol. 98, pp. 284-290, Feb. 2003.
Laurence, K., et al., "The Natural History of Hydrocephalus", Archives of Disease in Childhood, pp. 345-362, Apr. 1962.
McGirt, M., et al., "Cerebropsinal Shunt Survival and Etiology of Failures: A Seven-Year Institutional Experience", Pediatric Neurosurgery, vol. 36, No. 5, pp. 248-255, May 2002.
Patwardhan, N., et al., "Implanted Ventricular Shunts in the United States: The Billion Dollar a Year Cost of Hydrocephalus Treatment", Neurosurgery, vol. 56, No. 1, pp. 139-145, Jan. 2005.
Piatt, J., "Physical Examination of Patients with Cerebrospinal Fluid Shunts: Is There Useful Information in Pumping the Shunt?", Pediatrics, vol. 89, pp. 470-473, Mar. 1992.
Pitteti, R., "Emergency Department Evaluation of Ventricular Shunt Malfunction: Is the Shunt Series Really Necessary?", Pediatric Emergency Care, vol. 23, No. 3, pp. 137-141, Mar. 2007.
Sood S., et al., "Evaluation of Shunt Malfunction Using Shunt Site Reservoir", Pediatric Neurosurgery, vol. 32, pp. 180-186, 2000.
Ventureyra, E., et al., "A New Ventricular Catheter for the Prevention and Treatment of Proximal Obstruction in Cerebrospinal Fluid Shunts", Neurosurgery, Issue 34(5), pp. 924-926, May 1994.
Zorc, J., et al., "Radiographic Evaluation for Suspected Cerebrospinal Fluid Shunt Obstruction", Pediatric Emergency Care, vol. 18, No. 5, pp. 337-340, 2002.

\* cited by examiner

| Assembly Type | MA100 |
|---|---|
| Standard Diameters D | .030".050".070" .080" |
| Body Length L | 3/8" |
| Lead Length A | 24" |
| Tolerance | See Table |
| Wire Gauge | 28,30,32,38AWG |
| Standard Wire Insulation | *Heavy Isomid *Medical Grade PVC *Polyurethane with Nylon Overcoat |
| Body Material | Molded Plastic or Kapton Sleeve |
| Nominal R Values @ 25°C | 2252, 3000, 5000 10,000 Ohms |

THERMAL RESPONSE TIME (63% RESPONSE)

| Series | Still Air | Still Water* |
|---|---|---|
| MA100 Catheter Assembly | 15 sec. | 2.0 sec. |

*Response time provided is for assembly plunged from 25°C air to 5°C still water 100GG - Series, 100, .080" diameter molded plastic tip 28 gauge kynar insulated twisted pair

CEREBROSPINAL FLUID EVALUATION SYSTEM HAVING THERMAL FLOW AND FLOW RATE MEASUREMENT PAD USING A PLURALITY OF CONTROL SENSORS

CROSS-REFERENCE TO RELATED APPLICATIONS

This application is a Continuation application of, and takes the benefit under 35 U.S.C. §120 of, application Ser. No. 12/936,162 filed on Oct. 1, 2010, which in turn is a national stage application that claims the benefit under 35 U.S.C. §371 of International Application No. PCT/US2009/039146 filed on Apr. 1, 2009, which in turn takes its priority from U.S. Provisional Application No. 61/042,496 filed on Apr. 4, 2008 and also claims the benefit under 35 U.S.C. §120 and 37 CFR §1.78(a)(2)(ii) of U.S. application Ser. No. 12/055,990 (now abandoned) filed on Mar. 26, 2008, which in turn claims the benefit of U.S. Provisional Application No. 60/989,284 filed on Nov. 20, 2007, and of U.S. Provisional Application No. 60/941,827 filed on Jun. 4, 2007, and of U.S. Provisional Application No. 60/939,205 filed on May 21, 2007, and of U.S. Provisional Application No. 60/911,687 filed on Apr. 13, 2007, and all of whose entire disclosures are incorporated by reference herein.

BACKGROUND OF THE INVENTION

1. Field of Invention

The present invention generally relates to cerebrospinal fluid shunts and, more particularly, to a method and device for testing for the presence, absence and/or rate of flow in the shunt tubing implanted under the skin.

2. Description of Related Art

A cerebrospinal fluid (CSF) shunt includes a system of tubing that allows CSF to flow from a patient's brain to another part of the body (e.g., abdomen to relieve pressure in the brain). As a result, it is desirable to know, periodically, that the pathway of the CSF shunt remains unobstructed to permit CSF flow and what the flow rate is. It is also desirable to make these determinations non-invasively when quantifying the CSF flow.

The following describe different apparatus and methodologies that have been used to monitor, determine or treat body fluid flow, including CSF flow through a shunt.

"A Thermosensitive Device for the Evaluation of the Patency of Ventriculo-atrial Shunts in Hydrocephalus", by Go et al. (Acta Neurochirurgica, Vol. 19, pages 209-216, Fasc. 4) discloses the detection of the existence of flow in a shunt by placement of a thermistor and detecting means proximate the location of the shunt and the placement of cooling means downstream of the thermistor. The downstream thermistor detects the cooled portion of the CSF fluid as it passes from the region of the cooling means to the vicinity of the thermistor, thereby verifying CSF flow. However, among other things, the apparatus and method disclosed therein fails to teach or suggest an apparatus/method for quantifying the flow of the fluid through the shunt.

In "A Noninvasive Approach to Quantitative Measurement of Flow through CSF Shunts" by Stein et al., Journal of Neurosurgery, 1981, April; 54(4):556-558, a method for quantifying the CSF flow rate is disclosed. In particular, a pair of series-arranged thermistors is positioned on the skin over the CSF shunt, whereby the thermistors independently detect the passage of a cooled portion of the CSF fluid. The time required for this cooled portion to travel between the thermistors is used, along with the shunt diameter, to calculate the CSF flow rate. See also "Noninvasive Test of Cerebrospinal Shunt Function," by Stein et al., Surgical Forum 30:442-442, 1979; and "Testing Cerebropspinal Fluid Shunt Function: A Noninvasive Technique," by S. Stein, Neurosurgery, 1980 Jun. 6(6): 649-651. However, the apparatus/method disclosed therein suffers from, among other things, variations in thermistor signal due to environmental changes.

U.S. Pat. No. 4,548,516 (Helenowski) discloses an apparatus for indicating fluid flow through implanted shunts by means of temperature sensing. In particular, the apparatus taught by Helenowski comprises a plurality of thermistors mounted on a flexible substrate coupled to a rigid base. The assembly is placed on the skin over the implanted shunt and a portion of the fluid in the shunt is cooled upstream of the assembly. The thermistors detect the cooled portion of the fluid as it passes the thermistor assembly and the output of the thermistor is applied to an analog-to-digital converter for processing by a computer to determine the flow rate of the shunt fluid.

U.S. Pat. No. 6,413,233 (Sites et al.) discloses several embodiments that utilize a plurality of temperature sensors on a patient wherein a body fluid (blood, saline, etc.) flow is removed from the patient and treated, e.g., heated or cooled, and then returned to the patient. See also U.S. Pat. No. 5,494,822 (Sadri). U.S. Pat. No. 6,527,798 (Ginsburg et al.) discloses an apparatus/method for controlling body fluid temperature and utilizing temperature sensors located inside the patient's body.

U.S. Pat. No. 5,692,514 (Bowman) discloses a method and apparatus for measuring continuous blood flow by inserting a catheter into the heart carrying a pair of temperature sensors and a thermal energy source. See also U.S. Pat. No. 4,576,182 (Normann).

U.S. Pat. No. 4,684,367 (Schaffer et al.) discloses an ambulatory intravenous delivery system that includes a control portion of an intravenous fluid that detects a heat pulse using a thermistor to determine flow rate.

U.S. Pat. No. 4,255,968 (Harpster) discloses a fluid flow indicator which includes a plurality of sensors placed directly upon a thermally-conductive tube through which the flow passes. In Harpster a heater is located adjacent to a first temperature sensor so that the sensor is directly within the sphere of thermal influence of the heater.

U.S. Pat. No. 3,933,045 (Fox et al.) discloses an apparatus for detecting body core temperature utilizing a pair of temperature sensors, one located at the skin surface and another located above the first sensor wherein the output of the two temperature sensors are applied to a differential amplifier heater control circuit. The control circuit activates a heat source in order to drive the temperature gradient between these two sensors to zero and thereby detect the body core temperature.

U.S. Pat. No. 3,623,473 (Andersen) discloses a method for determining the adequacy of blood circulation by measuring the difference in temperature between at least two distinct points and comparing the sum of the detected temperatures to a reference value.

U.S. Pat. No. 3,762,221 (Coulthard) discloses an apparatus and method for measuring the flow rate of a fluid utilizing ultrasonic transmitters and receivers.

U.S. Pat. No. 4,354,504 (Bro) discloses a blood-flow probe that utilizes a pair of thermocouples that respectively detect the temperature of a hot plate and a cold plate (whose temperatures are controlled by a heat pump. The temperature readings are applied to a differential amplifier. Energization of the heat pump is controlled by a comparator that compares a references signal to the differential amplifier output that ensures that the hot plate does not exceed a safety level during use.

U.S. Patent Publication No. 2005/0171452 (Neff), which is owned by the same assignee as the present application, namely, Neuro Diagnostic Devices, Inc., and which is incorporated by reference herein, discloses a cerebral spinal fluid (CSF) shunt evaluation system that utilizes pairs of temperature sensors, each pair having an upstream and a downstream temperature sensor and whose outputs are analyzed for providing CSF flow rates when an upstream temperature source is applied to the patient.

U.S. Patent Publication No. 2005/0204811 (Neff), which is owned by the same assignee as the present application, namely, Neuro Diagnostic Devices, Inc., discloses a CSF shunt flow measuring system contains upstream and downstream temperature sensors embedded within the wall of a shunt with a temperature source located between the sensors and whose outputs are analyzed for providing CSF flow.

However, there remains a need to quickly and non-invasively determine the flow status or flow rate of a fluid in a subcutaneous tube.

All references cited herein are incorporated herein by reference in their entireties.

BRIEF SUMMARY OF THE INVENTION

An apparatus for evaluating cerebrospinal fluid (CSF) flow rate or flow status in a CSF shunt applied to the body of a patient for transmitting the CSF between first and second locations of the body. The apparatus comprises: a pad that is placed against the skin of a patient over the location of the CSF shunt, wherein the pad comprises a plurality of temperature sensors (e.g., fast response thermistors) that are aligned in a first direction (e.g., in a direction that is transverse to the CSF shunt) and wherein one of the plurality of temperature sensors is aligned with the CSF shunt and wherein each of the temperature sensors generates respective temperature data. The apparatus further comprises a sensor processing device (e.g., a CSF analyzer) that is electrically coupled to the pad for receiving temperature data from each of the temperature sensors, and wherein the sensor processing device uses the temperature data to determine a flow rate or flow status of the CSF through said shunt when a temperature source (e.g., an ice pack or cube) is applied to the pad.

A method for evaluating cerebrospinal fluid (CSF) flow rate or flow status in a CSF shunt. The method comprises: applying a plurality of temperature sensors (e.g., fast response thermistors) against the skin over the location of the CSF shunt and aligned in a first direction (e.g., in a direction that is transverse to the CSF shunt), and wherein only one of the plurality of temperature sensors is aligned with the CSF shunt; applying a temperature source (e.g., an ice pack or cube) over the CSF shunt and upstream of the plurality of temperature sensors for a predetermined period;
collecting temperature data from said plurality of temperature sensors after said predetermined period of time (e.g., 60 seconds) has elapsed; generating a resultant temperature signal; and determining a flow rate or flow status of the CSF through the shunt from said resultant temperature signal.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

This application incorporates by reference the disclosure of application Ser. No. 12/055,990, filed on Mar. 26, 2008 entitled CEREBRAL SPINAL FLUID EVALUATION SYSTEMS. The invention of the present application includes further improvements of the inventions disclosed in application Ser. No. 12/055,990.

Figure 1:
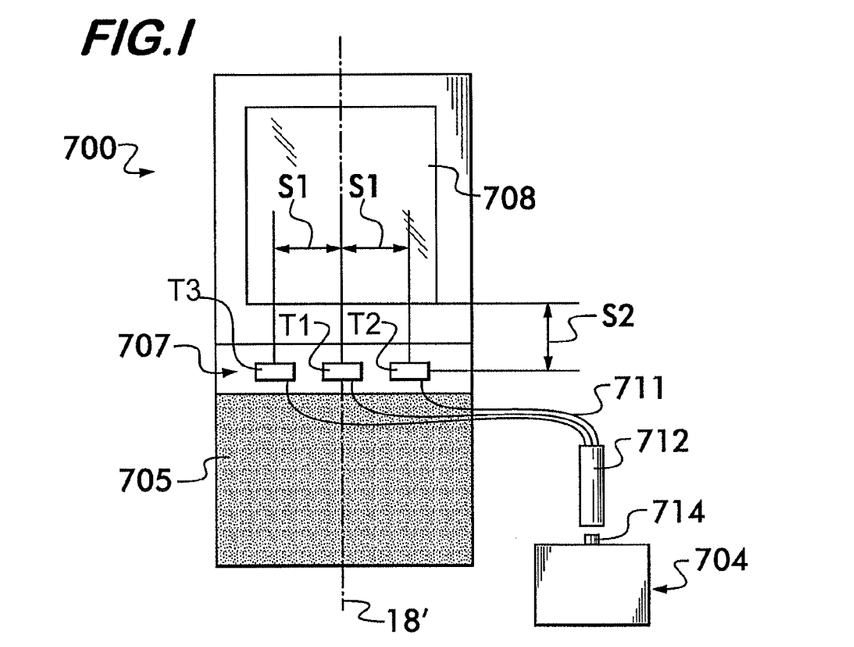
FIG. 1 shows a functional block diagram of the reverse side of a measurement pad connected to a CSF analyzer of the present invention.

Referring now to FIG. 1, there is shown a functional diagram of the system and method of the present invention 700. In particular, the invention 700 comprises a thermal flow measurement pad 702 which is in electrical communication with a CSF analyzer 704, also known as a sensor processing device (e.g., a processor with I/O). As will be discussed in detail later, the measurement pad 702 comprises a plurality of sensors, such as thermistors, which are maintained in the correct relative geometries by the measurement pad 702. The analyzer 704 also provides the sensor excitation. The measurement pad 702 improves the performance of methods for thermal measurement of CSF flow in implanted shunts. In particular, the measurement pad 702 provides substantially greater accuracy and repeatability. Additionally, the measurement pad 702 makes such flow and flow rate measurements substantially easier and more convenient. As with the invention of application Ser. No. 12/055,990, one of the key distinctions of the present invention 700 with respect to the prior art systems, is that the plurality of sensors are localized within the measurement pad 702. As shown in FIG. 1, the measurement pad 702 includes an electrical cable 711 having a connector 712 that couples to a mating connector 714 in the CSF analyzer 704.

As with application Ser. No. 12/055,990, the measurement pad 702 of the present invention is provided with at least one clear window 708 in order to permit accurate placement of the measurement pad 702 and the uniform application of a temperature source, e.g., a cooling means such as an ice cube or pack. It is preferable to use a "plastic ice" cube (which contains water) which avoids or minimizes leaking when compared to an ice cube. To use this embodiment of the measurement pad 702, a shunt tube 18 which is positioned below the patient's skin can be located by the physician and the patient's skin can be marked with a pen or other marking device in order to indicate the location of the shunt tube 18. The measurement pad 402 is then manipulated until the mark (not shown) appears in an aperture (also not shown; or, alternatively, a mark on the skin can be aligned with other indicia on the measurement pad 702).

Figure 3:
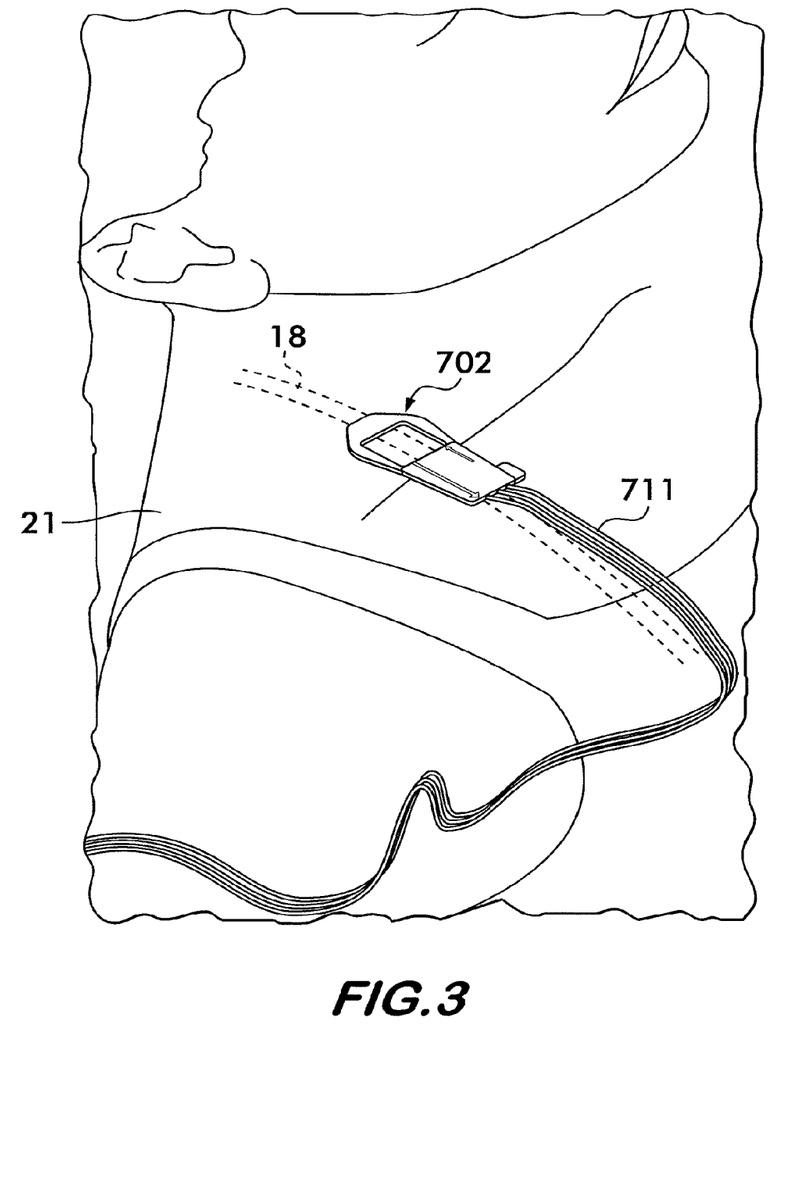
FIG. 3 shows how the measurement pad is placed on the patient's skin while being located over the shunt tube (shown in phantom) beneath the skin and electrically coupled the to the CSF analyzer (not shown)

The measurement pad 702 comprises three temperature sensors (e.g., thermistors), T1, T2 and T3, as shown in FIG. 1. When the measurement pad 702 is placed properly on the skin 21 and aligned with the shunt tube 18 (FIG. 3) located under the skin 21, the first temperature sensor T1 is aligned with the shunt tube's axis 18'. Temperature sensors T2 and T3 act as control temperature sensors and are aligned laterally, on opposite sides, with temperature sensor T1, as shown in FIG. 1. In particular, it has been determined that human skin transfers heat and cold in a non-homogenous manner. By using only the shunt-aligned temperature sensor T1 and a single control temperature sensor T2, when the temperature source, e.g., a cooling means such as an ice cube or pack is placed on the measurement pad 702, the sensor T1 and the control sensor T2 experience different amounts of coldness. As a result, the temperature changes will not be equal even if there is no flow in the shunt 18. To overcome this problem, the present invention 700 includes another control sensor T3 on the other side of the shunt 18, thereby establishing two control sensors T2 and T3, symmetrically positioned on both sides of the shunt, as indicated by the distance S1. By way of example only, the distance Si is approximately 8 mm from the shunt-aligned sensor T1. Also, each of the temperature sensors T1, T2 and T3 are positioned a distance S2 from the edge of the window 708. By way of example only, the distance S2 is approximately 8 mm.

To provide good contact with the skin, the skin-contact surface 705 of the measurement pad 702 is treated with an adhesive (e.g., 3M Adhesive Acrylate for medical/surgical use). However, because this adhesive has some thermal conductive properties which would interfere with temperature sensor operation, the temperature sensors T1, T2 and T3 are secured to the pad 702 but at a location 707 of the surface 705 that is void of any of this adhesive.

The resultant temperature signal is given by:

$$T1 - \frac{(T2 + T3)}{2}$$

where T1 is the shunt-aligned temperature sensor signal and T2 and T3 are the respective control temperature sensor signals, respectively.

Figure 2:
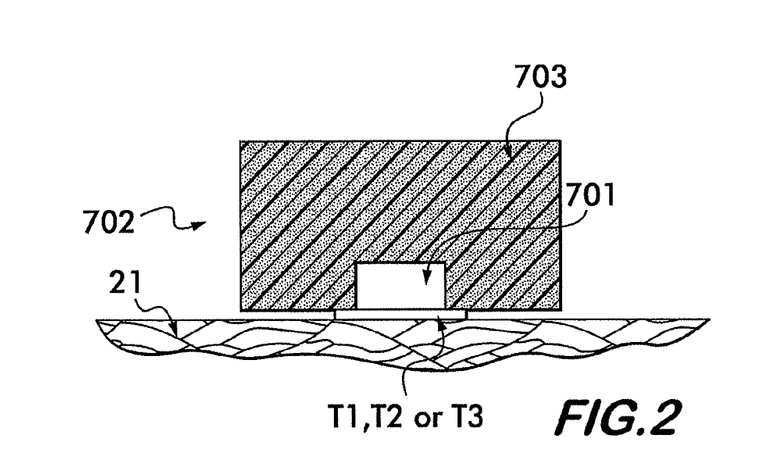
FIG. 2 is an enlarged cross-sectional view of the measurement pad of the present invention placed on the skin of a living being.
Figure 5:
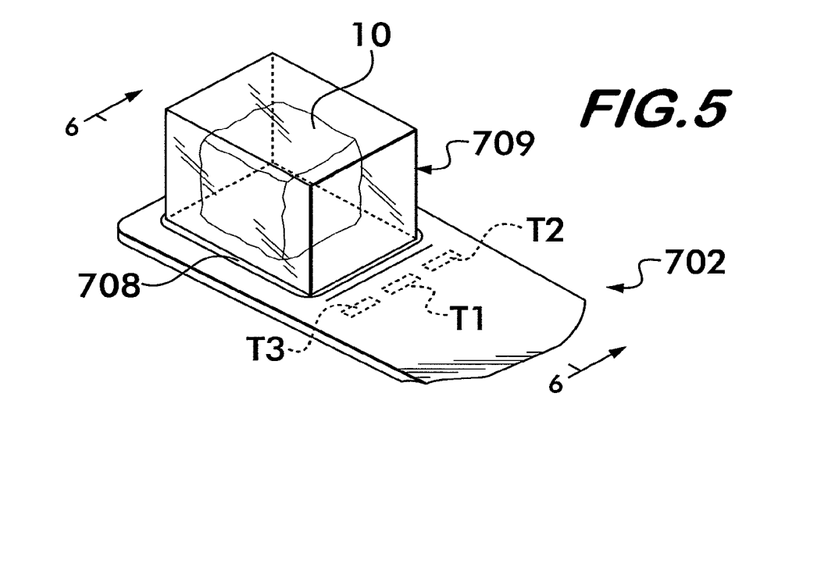
FIG. 5 is an isometric view of the measurement pad using an insulation housing that encloses an ice source, e.g., an ice cube, for providing a temperature source.
Figure 6:
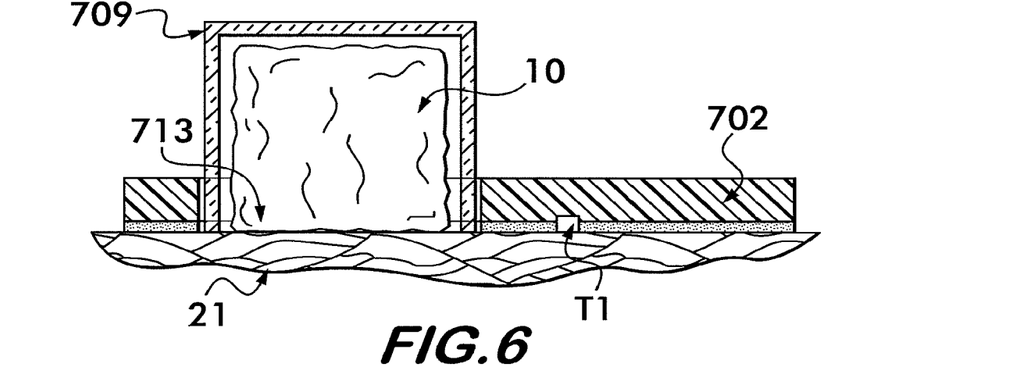
FIG. 6 is a side cross-sectional view of the measurement pad using the insulation housing taken along line 6-6 of FIG. 5.

It has been further determined that coldness or "coolant" can transfer cold via air to the temperature sensor pad. Thus, to overcome this issue, insulation of the sensors T1, T2 and T3 has been introduced. In particular, the sensors T1, T2 and T3 do not contact the measurement pad 702 on the entire surface but are placed in air bubbles or domes 701 within a thermal insulator 703 (e.g., polystyrene foam) and then glued onto the ends of the measurement pad 702. It should be noted that the thermal insulator shown in FIG. 2 is an exaggerated view of the thickness of the thermal insulator 703. Furthermore, to prevent such a transfer through the air, an insulation cup/housing 709 is provided that covers or contains the temperature source (e.g., ice cube 10) so as to prevent or at least minimize such air transfer. By way of example only, as shown in FIGS. 5-6, the insulation housing or enclosure 709 comprises a cube form that covers insulates the ice cube 10 in all directions except along the bottom surface 713 which is open to permit direct contact with the skin 21 through the window 708. This permits the controlled application of a temperature "pulse" or "spike" or "wave" only at the skin surface 21 over the shunt 18. Without the insulated enclosure or housing 709, the "cold wave" generated by the ice cube 10 generates a fair amount of noise/inaccuracy that would be experienced by the sensors T1, T2 and T3 through the air. It should be noted that the cube form of the enclosure/housing 709 is by way of example only and that it may take on any shape to enclose or house the temperature source, whatever its shape, to prevent the transfer of the temperature pulse, wave or spike through the air but rather permit transfer only through an opening in the enclosure/housing that is in contact with the skin 21.

Figure 4:
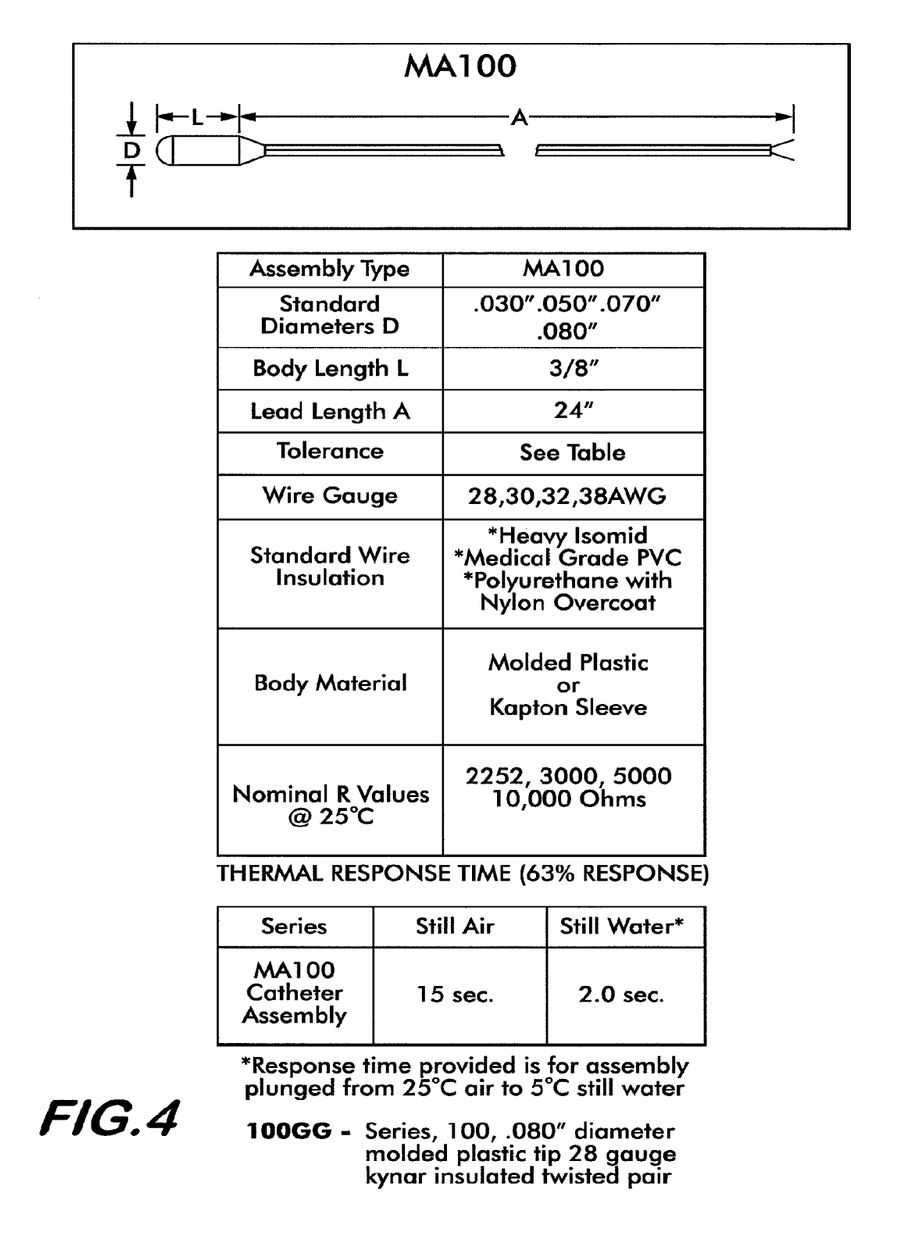
FIG. 4 is a specification sheet of an exemplary fast response thermistor for use in the measurement pad of the present invention.

It should be understood that the type of thermistor used for the temperature sensors T1, T2 and T3 must be fast response thermistors, i.e., a time constant of <5 seconds. This is important because the thermistor must be able to track the actual temperature without an appreciable time lag. By way of example only, FIG. 4 is specification sheet of an exemplary fast response thermistor that can be used for the thermistors T1, T2 and T3 in the measurement pad 702. As can be seen from FIG. 4, the MA100 Catheter Assembly has a thermal response time in still water of 2.0 seconds. Another exemplary thermistor is the GE NTC thermistor.

The following discussion is directed to the operation of the present invention 400 which uses all three thermistors, T1, T2 and T3.

As discussed previously, the present invention 700 is provided with the shunt-aligned thermistor T1 for determining the existence of CSF flow through the shunt tubing 18, and determining the flow status (i.e., flow or no flow) and the flow rate of the CSF flow F through the shunt tubing 18. The shunt-aligned sensor T1 measures the temperature as the cooling pulse passes from the cooling means and into the CSF in the shunt tubing 18. Also, the control thermistors T2 and T3 are used, along with the shunt-aligned thermistor T1, to permit the calculation of error signals due to background effects such as body temperature and ambient temperature. The error signals within the CSF shunt evaluation system 700 can be used to provide a more accurate determination of the CSF flow status or rate through the shunt tubing 18. It is this conduction through the skin that is detected by the control thermistors T2 and T3. The alignment assures that the shunt-aligned thermistor T1 detects the temperature delta via the shunt tubing 18 while the temperature delta propagated via the skin is detected by the control sensors T2 and T3. The control thermistors T2-T3 thus provide electrical output signals representative of the detected temperature delta transmitted through the skin 21. The output signals from the control thermistors T2/T3 permit control readings to be performed by the CSF evaluation system 700 for error correction of the flow rate calculations that can be obtained using the thermistors T1, T2 and T3. All of the thermistors T1, T2 and T3 must be equalized for static and dynamic responses In accordance with the temperature profiles shown in FIG. 7, the depth of the temperature profiles is a function of the CSF flow, i.e., the faster the CSF flow, the deeper the "dip" in the temperature profile. The CSF evaluation system 700 operates in a similar manner but with the additional improvements.

Figure 7:
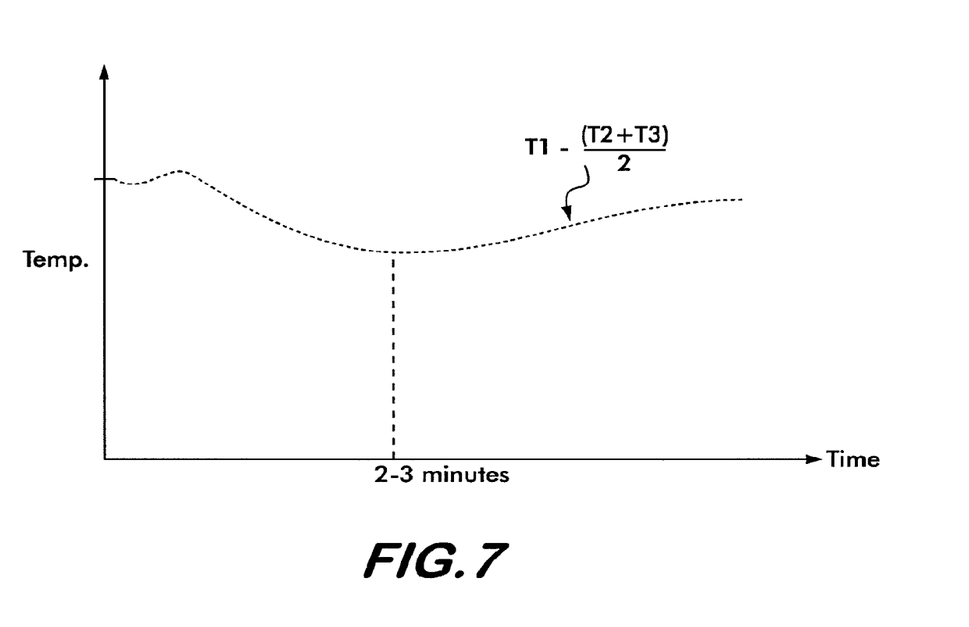
FIG. 7 depicts an exemplary temperature profile of test data where the control sensors data is subtracted from the shunt-aligned sensor data.

Using a sampling rate of approximately 10 samples/sec (down to a minimum of 1 sample/sec), the three thermistors begin obtaining temperature data once the test begins (see FIG. 7). As shown in FIG. 7, the CSF analyzer 704 determines the temperature profile the temperature sensors. The subtraction of the control thermistors' T2 and T3 data is critical because it is subjected to the same effects as the shunt-aligned thermistor T1. By doing this, the unwanted effects (e.g., chilling of skin, flushing effect, etc.) are cancelled out of the temperature data. The positioning of the control thermistors T2 and T3 are such that they are "close enough" to detect the cold pulse through the skin/tissue but "far enough" away from the shunt tubing 18 to not detect the cold pulse being propagated through the CSF in the shunt tubing 18. A typical temperature "trough" (see FIG. 7) is approximately 2-3 minutes for a test run of approximately 9 minutes, with the algorithm itself (the CSF analyzer 704) taking approximately 6 minutes.

It is preferable to make the measurement pad 702 a one-time use device and include an interlock that prevents the re-use of the measurement pad 702. As mentioned earlier, the measurement pad 702 includes an electrical cable 711/connector 712 that couples to a mating connector 414 in the CSF analyzer. The electrical connector 712 may include an integrated circuit that detects the use and should the connector 712 ever be reconnected to a CSF analyzer 704, the CSF analyzer 704 provides an indication to the operator of the prior use and prevents the test from commencing. In particular, each measurement pad 702 may contain an electronic code which matches codes logged into the accompanying CSF analyzer 704. Thus, the CSF analyzer 704 can be programmed to operate only with selected measurement pads 702. For example, the thermistors may themselves contain the code or information.

It has also been found that it is ideal to have the patient placed in a supine position for a predetermined period of time (e.g., 5 minutes). This permits the ventricle to refill. Once the measurement pad 702 is warmed up and the testing is ready to begin, the patient is then permitted to come to a sitting position to permit gravity to accelerate the CSF flow. Attempting to conduct the test on patient who has been in a standing or seated (upright) position drains the cranium and results in a no flow condition, which is normal.

As mentioned earlier, an optimal distance (e.g., 8 mm) exists between the ice or other cooling means and the temperature sensors T1, T2 and T3. Furthermore, the accuracy of the test results provided by the measurement pad 702 is enhanced by tight and precise distances between the cooling means and the temperature sensors T1, T2 and T3. Therefore, the location of the window 708 on the measurement pad 702, relative to the temperature sensors T1, T2 and T3, is adapted to reliably provide the optimal distance between the cooling means and these sensors T1, T2 and T3 when the cooling means is placed on the window 708 and centered. Thus, when the cooling means (e.g., ice cube 10) is placed on the window 708 of the pad, it is located at the optimal distance from the temperature sensors. The uniform or symmetric application of the cooling pulse is important for the detection mechanism to work properly and thus a variety of window 708 shapes are encompassed by the present invention 700. One exemplary configuration is to have a circular-shaped window 708 (e.g., a 1 inch radius). When the cooling means is applied, it is applied for 60 seconds and then removed from the window 708. However, before applying the cooling means, a measurement pad 702 "warm up" period (e.g., a few minutes) occurs, i.e., the pad 702 is applied to the skin and permitted to reach the skin temperature. Once that skin temperature is achieved, then the cooling means is applied for 60 seconds. It has also been determined that the amount of pressure applied to the cooling means when placed in the window needs to be uniform.

In order to provide accurate readings, it is necessary to verify certain criteria, for example:
1) verifying that the temperature data reaches a predetermined value within a certain time limit (e.g., within 5 minutes). If it takes more than 5 minutes to reach that predetermined value, there is something incorrect in the test setup. For example, a typical temperature spike or wave or pulse movement is achieved in approximately 2-3 minutes (see FIG. 7).
2) Checking the smoothness of the curve. A spike in the data is most probably an undesirable movement of the measurement pad 702.
3) A threshold should be satisfied:

$$\text{threshold} = T1 - \frac{T2 + T3}{2} > 0.2$$

4) Slope checks (temperature data must decrease then rise as shown in FIG. 7).
5) Integral checks-using the area under the curve in relation to flow rate.
6) Gradients (verifying the gradients in the temperature drops in relation to flow rate).

It should also be noted that it is within the broadest scope of the present invention to include a recharging stand for the CSF analyzer 704 (when it is a hand-held device) that can communicate with a personal computer.

While the invention has been described in detail and with reference to specific examples thereof, it will be apparent to one skilled in the art that various changes and modifications can be made therein without departing from the spirit and scope thereof.

What is claimed is:

1. An apparatus for evaluating cerebrospinal fluid (CSF) flow rate or flow status in a CSF shunt applied to the body of a patient for transmitting said CSF between first and second locations of said body, said apparatus comprising:
a single pad that is adapted to be placed against the skin of a patient over the location of the CSF shunt and comprising an opening that is adapted to apply a temperature source against the skin and a temperature pulse into the CSF, said pad comprising a plurality of temperature sensors and wherein one of said plurality of temperature sensors is configured to be aligned with the CSF shunt, each of said temperature sensors configured to generate respective temperature data related to movement of said temperature pulse in the CSF or in surrounding skin; and
a sensor processing device that is electrically coupled to said pad for receiving temperature data from each of said temperature sensors, said sensor processing device determining a flow rate or flow status of said CSF through said shunt based upon said temperature data when said temperature source is applied to said opening.

2. The apparatus of claim 1 wherein at least a second one of said plurality of temperature sensors is a control temperature sensor, said at least a second one of said plurality of temperature sensors is configured not to be aligned with the CSF shunt.

3. The apparatus of claim 2 wherein said at least a second one of said plurality of temperature sensors comprises a temperature sensor on one side of said temperature sensor configured to be aligned with the CSF shunt and another temperature sensor on the other side of said temperature sensor configured to be aligned with the CSF shunt.

4. The apparatus of claim 3 wherein said one of said plurality of temperature sensors configured to be aligned with the CSF shunt and said temperature sensor on one side of said sensor configured to be aligned with the CSF shunt and said another temperature sensor on the other side of said temperature sensor configured to be aligned with the CSF shunt are configured to be aligned transversely with respect to the CSF shunt.

5. The apparatus of claim 1 further comprising an insulated enclosure, said insulated enclosure adapted for receiving said temperature source and wherein said insulated enclosure, along with said temperature source, is positioned within said opening in said pad for applying said temperature pulse against the skin over the CSF shunt and preventing transfer of said temperature pulse through the air.

6. The apparatus of claim 1 wherein said temperature source is an ice cube.

7. The apparatus of claim 1 wherein said flow rate or flow status comprises a resultant temperature signal formed by said sensor processing device by comparing said temperature data from said one of said plurality of temperature sensors configured to be aligned with the CSF shunt with said temperature data from the other of said plurality of temperature sensors that are configured to be not aligned with the CSF shunt.

8. The apparatus of claim 7 wherein said plurality of temperature sensors comprises three temperature sensors and wherein said temperature data of said one (T1) of said plurality of temperature sensors configured to be aligned with the CSF shunt is compared to said temperature data of said one (T2) of said other of said plurality of temperature sensors configured to be not aligned with the CSF shunt, and wherein said temperature data of said one (T1) of said plurality of temperature sensors configured to be aligned with the CSF shunt is also compared with said temperature data of another one (T3) of said plurality of temperature sensors configured to be not aligned with the CSF shunt.

9. The apparatus of claim 1 wherein said temperature source is an ice cube.

10. The apparatus of claim 1 wherein said opening is spaced away from said plurality of temperature sensors by 8 mm.

* * * * *